United States Patent [19]

Cincotta et al.

[11] Patent Number: 5,700,795

[45] Date of Patent: Dec. 23, 1997

[54] ADMINISTRATION OF PIRENZEPINE, METHYL SCOPOLAMINE AND OTHER MUSCARINIC RECEPTOR ANTAGONISTS FOR TREATMENT OF TYPE II DIABETES

[75] Inventors: Anthony H. Cincotta, Andover, Mass.; Albert H. Meier, Baton Rouge, La.; John M. Wilson, Charlestown, Mass.

[73] Assignees: The General Hospital Corporation, Boston, Mass.; The Board of Supervisors of Louisiana State University and Agricultural and Mechanical College, Baton Rouge, La.

[21] Appl. No.: 458,085

[22] Filed: Jun. 1, 1995

Related U.S. Application Data

[63] Continuation of Ser. No. 263,607, Jun. 20, 1994, which is a continuation-in-part of Ser. No. 995,292, Dec. 22, 1992, Pat. No. 5,585,347, which is a continuation-in-part of Ser. No. 719,745, Jun. 24, 1991, Pat. No. 5,344,832, which is a continuation of Ser. No. 463,327, Jan. 10, 1990, abandoned, which is a continuation-in-part of Ser. No. 192,332, May 10, 1988, abandoned.

[51] Int. Cl.$^6$ .................... A61K 31/545; A61K 31/55; A61K 31/44; A61K 31/35
[52] U.S. Cl. .................... 514/200; 514/218; 514/220; 514/291; 514/454; 514/866
[58] Field of Search .................... 514/200, 218, 514/220, 291, 454, 866

[56] References Cited

U.S. PATENT DOCUMENTS

| | | | |
|---|---|---|---|
| 3,074,847 | 1/1963 | Bigsley | 514/271 |
| 3,752,888 | 8/1973 | Fluckinger et al. | 514/250 |
| 3,755,328 | 8/1973 | Stadler et al. | 544/346 |
| 4,219,555 | 8/1980 | Rucman | 514/250 |
| 4,239,763 | 12/1980 | Milavec | 514/250 |
| 4,659,715 | 4/1987 | Meier | 514/288 |
| 4,749,709 | 6/1988 | Meier | 514/288 |
| 4,783,469 | 11/1988 | Meier | |
| 5,006,526 | 4/1991 | Meier | 514/250 |

FOREIGN PATENT DOCUMENTS

| | | |
|---|---|---|
| 890369 | 3/1982 | Belgium . |
| 2192541 | 1/1988 | United Kingdom . |

OTHER PUBLICATIONS

Harel et al., *Proc. La. Acad. of Sci.* 38:125, 1975.
Komorowski et al., *Aliment. Nutr. Metab.* 1(4):293, 1980.
Larsson et al., *La Kartidningen (Sweden)* 82(50):4425, 1985.
Martin et al., *The Condor* 75:369–374, 1973.
Martin et al., *Chronobiology*, "Hormonal Control of Orientation in the White–Throated Sparrow, *Zonotrichia albicollis*." pp. 641–646, 1974.
Martin et al., *Proc. La. Acad. of Sci.* 38:127, 1975.
Martin et al., *Am. Zoologist* 18(3):672, 1978.
Martin, D., "Hormonal Regulation of Migratory Orientation in the White–Throated Sparrow, *Zonotrichia albicollis*." Diss. LSU, 1974.

Martin, D., "Factors Influencing the Circadian Rhythm of Locomotor Activity in the Anabatoid Fish, *Tirchogaster Trichopterus sumatramus*." Thesis. Sam Houston State College, 1969.
Meier et al., *Gen & Comp. Endocrinol.* Supp 3:499–508, 1972.
Meier et al., *Gen & Comp. Endocrinol.* 26:253–258, 1975.
Meier et al., *Physiol. Zool.* 41(1):95–103, 1968.
Chemical Abstracts, vol. 118, No.21 issued 24 May 1993, Parkarinen et al., "Comparison of the effect of scopolamine and methylscopolamine on the performance of a fixed-ratio discrimination in squirrel monkeys" see p. 70, col. 1, abstract No. 205134y, Pharmacol., Biochem. Behav., 44(4), 815–19.
Atiea et al., *J. Clin. Endocrinol.* 69: 390–5, 1989.
Barnett et al., *Postgraduate Med. J.* 56: 11–14, 1980.
Bell et al., *Atherosclerosis* 36: 47–54, 1980.
Bevan et al., *Clinical Endocrinol.* 36: 85–91, 1991.
Birdsall et al., *Trends Pharmacol. Sci.* 4: 459, 1983.
Blackburn, *N.E.J.M.* 309: 426–8, 1983.
Cincotta et al., *Metabolism* 40: 639–644, 1991.
Cincotta et al., *Amer. J. Physiol.* 264: E285–93, 1993.
Cincotta et al., *Chronobiol. Int'l* 10: 244–258, 1993.
Coiro et al., *J. Endocrinol. Invest.* 9: 27–30, 1986.
Coruzzi et al., *Arch. Int. Pharmocodyn. Ther.* 302: 232, 1989.
Coviezel et al., *Acta Diabetol. Lat.* (Italy) 26: 133–45, 1989.
Curtis–Prior et al., *Experientia* 35: 1430–1, 1979.
Davidson et al., *Diabetes* 37: 166–71, 1988.
Davidson et al., *Diabetes Care* 13: 813–4, 1990.
Davis et al., *Psychoneuroendocrinology* 7: 347–54, 1982.
El–Denshary et al., *Life Sciences* 40: 1531–5, 1987.
Fears, *Biochem. Pharmacol.* 33: 219–228, 1984.
Grigoriev et al., *Aviat. and Environ. Med.* 59: 301–5, 1988.
Harter et al., *Dev. Endocrinol.* 2: 331–49, 1978.
Haisenleder et al., *Proc. Soc.. Exp. Biol. Med.* 187: 341–9, 1988.
Illingworth & Conner in *Endocrinology & Metabolism*, Mc–Graw–Hill, New York, 1987.
Kawashima et al., *Gen. Pharmacol.* 21: 17, 1990.
Lambrecht et al., *Trends Pharmacol Sci.* 10 (Suppl): 60, 1989.
Martin et al., *Neuroendocrinology* 52: 9–14, 1990.

(List continued on next page.)

*Primary Examiner*—Kevin E. Weddington
*Attorney, Agent, or Firm*—Darby & Darby

[57] ABSTRACT

Disclosed are methods for improving various aberrant metabolic indices in mammals including humans by administration of muscarinic (particularly M1) receptor antagonists alone or in combination with prolactin inhibiting compounds. Preferably the administration takes place at a predetermined time (or, if a combination of muscarinic receptor antagonist and prolactin inhibitor is used, at different predetermined times) during a 24-hour period when the administration is effective (or its effect more pronounced). The invention has application in the treatment of lipid and glucose metabolism disorders.

8 Claims, 1 Drawing Sheet

OTHER PUBLICATIONS

Martina et al., *J. Clin Endocrinol.* 68: 392–6, 1989.
Meier et al., *Proc. Soc. Chronoendocrinol.*, in press.
Mendelson et al., *J. Clin Invest.* 61: 1683–90, 1978.
Negato et al., *Comp. Biochem. Physiol.* 106: 251–5, 1993.
Noma et al., *Atherosclerosis* 49: 1, 1983.
Ostinson et al., *Endocrinol.* 121: 1705–10, 1987.
Pietschmann et al., *Acts Endocrinol. (Copenh)* 117: 315–9, 1988.
Poland et al., *Biol. Psychiatry* 25: 403–12, 1989.
Risch et al., *Psychoneuroendocrinology* 11: 221–30, 1986.
Salans in *Endocrinology & Metabolism*, 2 ed., McGraw–Hill, New York 1987, pp. 1203–1244.
Stasiewicz et al., *Acta Medica Hungarica* 46: 189–95, 1989.
Thomas et al., *Sem. Hop. Paris* 53: 1857–62, 1977.
Thompson, *Br. Heart J.* 51: 585–8, 1989.
Williams, *Textbook of Endocrinology*, 1974, pp. 904–916.
Zaccoria et al., *Eur. J. Clin. Pharmacol.* 27: 701–5, 1985.
Bartness et al., *J. Exp. Zoology* 244: 437–454, 1987.
Berle, *Acta Endocr. Suppl.* 173, Abstract No. 104, 1973.
Burns, et al., *Rev. Chronopharmacology* 5:57–60, 1988.
Cincotta et al., *J. Endocr.* 103:141–146, 1984.
Cincotta et al., *J. Endocr.* 106:177–181, 1985.
Cincotta et al., *J. Endocr.* 106:173–176, 1985.
Cincotta et al., *Experientia* 43: 416–417, 1987.
Cincotta et al., *Ann Nutr Metab* 33:305–14, 1989.
Cincotta et al., *Horm. Metabol. Res.* 21:64–68, 1989.
Cincotta et al., *J. Endocrinology* 120:385–391, 1989.
Cincotta et al., *Life Sciences* 45:2247–2254, 1989.
Eisemann et al., *J. of Animal Sci.* 59(1)86–94, 1984.
Eisemann et al., *J. of Animal Sci.* 59(1)95–104, 1984.
Emata et al., *J. Exp. Zoology* 233:29–34, 1985.
Gnudi et al., *Acta Diabetologica Latina* 14:119–128, 1977.
Horseman et al., *General and Comparative Endocrinology* 38:269–274, 1979.
Horseman et al., *J. Endocr.* 82:367–372, 1979.
Iranmanesh et al., *J. Clin. Endocrin & Metabo.* 71: 73–7, 1990.
Joseph et al., *J. Exp. Zool.* 178(1):59–62, 1971.
Landgraf et al., *Proc. German Med. Soc.* 82nd Convention, Part II, Apr. 25–29, 1976.
Lee et al., *J. of Exp. Zool.* 166(3):307–316, 1967.
Lobato et al. *Mol. and Cell. Biochem.* 67:19–23, 1985.
Meier et al., *Gen. & Comp. Endocrin.* 8(1):110–114, 1967.
Meier, *Gen. & Comp. Endocrin. Supp.* 2:55–62, 1969.
Meier et al., *Proc. Soc. Exp. Biol. and Med.* 133 (4):113–16, 1970.
Meier et al., *Gen. & Comp. Endocrin.* 17: 311–8, 1971.
Meier et al., *Proc. Soc. for Exp. Bio. & Med.* 137:408–415, 1971.
Meier et al., *Science* 173: 1240–42, 1971.
Meier et al., *General and Comparative Endocrinology* Suppl. 3:499–508, 1972.
Meier, *Amer. Zoology*, 15 : 905–916, 1975.
Meier et al., *Amer. Zool.* 16 : 649–659, 1976.
Meier et al., *Amer. J. of Physiology* 232(2) :E193–E196, 1977.
Meier et al., *Compar. Endocrin.* 141–44, 1978.
Meier et al., *Current Ornithology* 2 : 303–343, 1984.
Meier et al., *Transactions of the American Fisheries Society* 113: 422–431, 1984.
Meier et al., *Experientia* 48: 248–53, 1992.
Miller et al., *J. Interdiscipl. Cycle Res.* 14(1) : 75–84, 1983.
Miller et al., *J. Interdiscipl. Cycle Res.* 14(2) : 85–94, 1983.
Ottenweller et al., *Life Science* 28: 1033–1040, 1980.
Southern et al., *J. Anim. Sci.* 68:931–936, 1990.
Spieler et al., *Gen. & Comparative Endocrinology* 29:156–160, 1976.
Spieler et al., *Life Sciences* 22:255–258, 1997.
Wheeland, et al., *Comp. Biochem. Physiol.* 53B; 379–385, 1976.
Wilson et al., *Chronobiology Int'l* 6(2) :113–121, 1989.3:189–195, 1989.

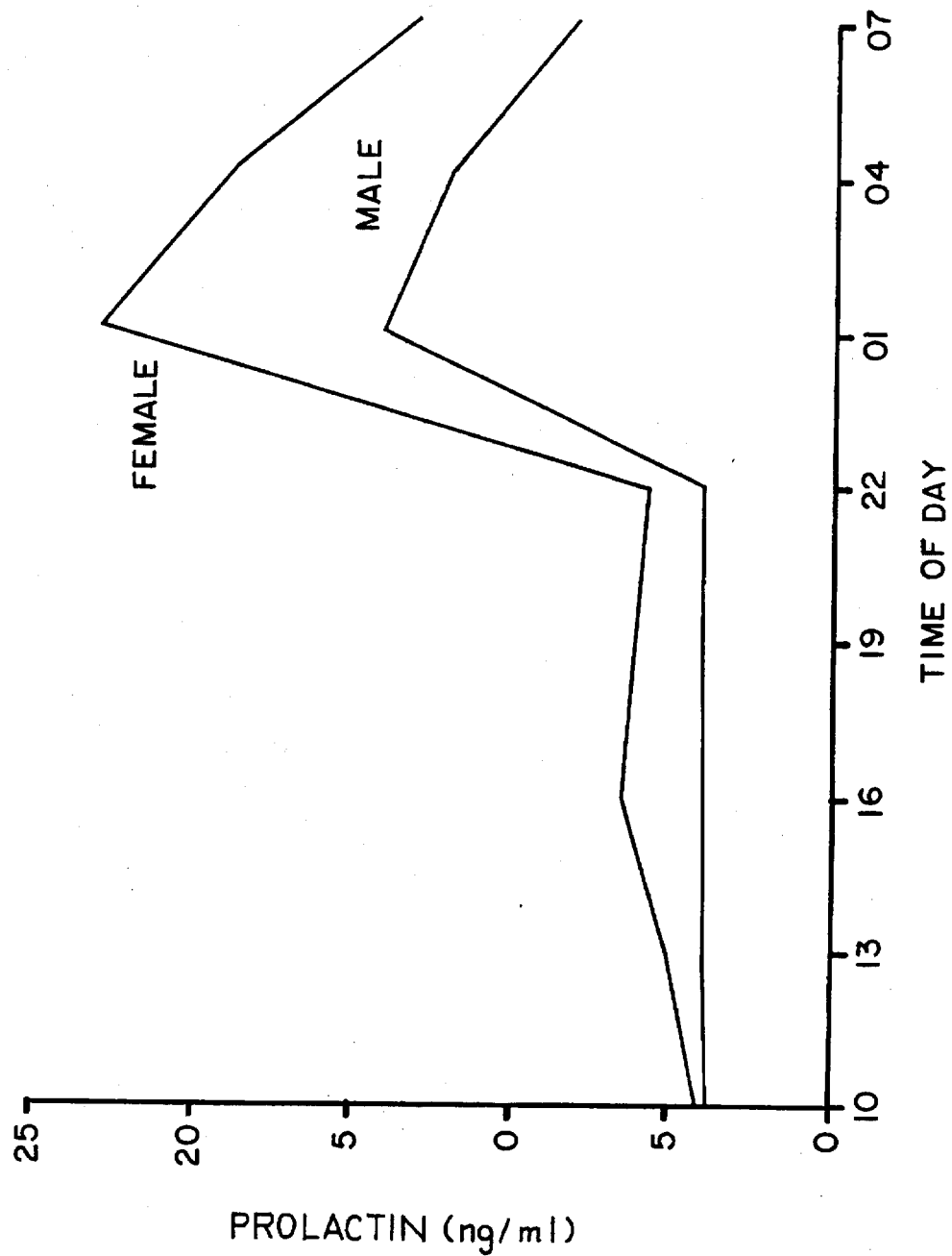

ADMINISTRATION OF PIRENZEPINE, METHYL SCOPOLAMINE AND OTHER MUSCARINIC RECEPTOR ANTAGONISTS FOR TREATMENT OF TYPE II DIABETES

RELATED APPLICATIONS

This is a continuation of application Ser. No. 08/263,607, filed Jun. 20, 1994 which is a continuation-in-part of U.S. application Ser. No. 07/995,292, filed Dec. 22, 1992, now U.S. Pat. No. 5,585,347, which is a continuation-in-part of U.S. application Ser. No. 07/719,745 filed Jun. 24, 1991, now U.S. Pat. No. 5,344,832, in turn a continuation-in-part of Ser. No. 07/463,327, filed Jan. 10, 1990, (now abandoned), itself a continuation-in-part of Ser. No. 07/192,332 filed May 10, 1988 (abandoned in favor of its Rule 62 continuation, Ser. No. 07/999,685 abandoned in favor of application Ser. No. 08/287,066, now U.S. Pat. No. 5,496,803), all by Anthony H. Cincotta and Albert H. Meier.

FIELD OF THE INVENTION

This invention relates to methods for the reduction in a subject, vertebrate animal or human, of at least one of the following indices of metabolism: body fat and more generally lipid stores, insulin resistance, hyperinsulinemia, hyperlipidemia, hyperlipoprotein-emia (such as chylomicrons, VLDL and LDL), and/or the increase in said subject of plasma HDL, and, more generally, the improvement of metabolism disorders, especially those associated with obesity, atherosclerosis and Type II diabetes. The methods comprise administration or timed administration of pirenzepine, methyl scopolamine, and other muscarinic M1 receptor antagonists, alone or in combination with a prolactin inhibitor, preferably a prolactin inhibitor that is also a dopamine agonist.

BACKGROUND OF THE INVENTION

Obesity and Lipid Metabolism Disorders—Body Fat Loss

In humans obesity can be defined as a body weight exceeding 20% of the desirable body weight for individuals of the same sex, height and frame (Salans, L. B., in *Endocrinology & Metabolism*, 2d Ed., McGraw-Hill, New York 1987, pp. 1203–1244; see also, R. H. Williams, *Textbook of Endocrinology*, 1974, pp. 904–916). In other animals (or also in humans) obesity can be determined by body weight patterns correlated with prolactin profiles given that members of a species that are young, lean and "healthy" (i.e., free of any disorders, not just metabolic disorders) have daily plasma prolactin level profiles that follow a regular pattern that is highly reproducible with a small standard deviation.

Obesity, or excess fat deposits, correlate with and may trigger the onset of various lipid metabolism disorders, e.g. hypertension, Type II diabetes, atherosclerosis, etc.

Even in the absence of clinical obesity (according to the above definition) the reduction of body fat stores (notably visceral fat stores) in man especially on a long-term or permanent basis would be of significant benefit, both cosmetically and physiologically.

The reduction of body fat stores in domestic animals (as well as pets) especially on a long-term or permanent basis would also obviously be of considerable economic benefit to man, particularly since farm animals supply a major portion of man's diet; and the animal fat may end up as de novo fat deposits in man.

Whereas controlled diet and exercise can produce modest results in the reduction of body fat deposits, prior to the cumulative work of the present inventors (including the prior co-pending patent applications and issued U.S. patents referred to below), no truly effective or practical treatment had been found for controlling obesity or other lipid metabolism disorders.

Hyperlipoproteinemia is a condition in which the concentration of one or more of cholesterol- or triglyceride-carrying lipoproteins (such as chylomicrons, very low density lipoproteins or VLDL and low-density lipoproteins or LDL) in plasma exceeds a normal limit. This upper limit is generally defined as the ninety-fifth percentile of a random population. Elevated levels of these substances have also been positively correlated with atherosclerosis and the often resulting cardiac infarction, or "heart attack", which accounts for approximately half of all deaths in the United States. Strong clinical evidence has been presented which correlates a reduction in plasma lipoprotein concentration with a reduced risk of atherosclerosis (Noma, A., et al., *Atherosclerosis* 49:1, 1983; Illingworth, D. and Conner, W., in *Endocrinology & Metabolism*, McGraw-Hill, New York 1987). Thus, a significant amount of research has been devoted to finding treatment methods which reduce levels of plasma cholesterol and triglycerides.

Another subset of the plasma lipoproteins found in vertebrates are high density lipoproteins, or HDL. HDL serve to remove free cholesterol from the plasma. A high HDL concentration as a percentage of total plasma cholesterol has been associated with a reduced risk of atherosclerosis and heart disease. Thus HDL are known in the lay press as "good" cholesterol. Therefore, therapeutic strategies involve attempts both to reduce plasma LDL and VLDL content (that is, reduce total plasma cholesterol), and to increase the HDL fraction of total plasma cholesterol. Several lines of research indicate that simply increasing HDL is of benefit even in the absence of LDL or VLDL reduction: Bell, G. P. et al., *Atherosclerosis* 36:47–54, 1980; Fears, R., *Biochem. Pharmacol.* 33:219–228, 1984; Thompson, G., *Br. Heart J.* 51:585–588, 1989; Blackburn, H. *N.E.J.M.* 309:426–428, 1983.

Current therapies for hyperlipoproteinemias include a low fat diet and elimination of aggravating factors such as sedentary lifestyle. If the hyperlipoproteinemia is secondary (i.e. incident to e.g. a deficiency of lipoprotein lipase or LDL receptor, various endocrine pathologies, alcoholism, renal disorders, hepatic disorders) then control of the underlying disease is also central to treatment. Hyperlipoproteinemias are also treated with drugs, which usually alter the levels of particular components of the total plasma cholesterol, as well as reduce the total plasma lipid component. Among the most recently introduced drugs to treat hyperlipoproteinemia .is lovastatin (MEVACOR®) which selectively inhibits an enzyme involved in cholesterol production, 3-hydroxy-3-methylglutaryl coenzyme A (HMG-CoA) reductase. This drug specifically reduces total cholesterol and can cause a modest (5–10%) increase in HDL concentrations. However, benefits from these therapies vary from subject to subject.

Moreover, use of the HMc-CoA enzyme inhibitor is sometimes accompanied by side effects such as liver toxicity, renal myoglobinuria, renal shutdown, and lenticular opacity. The risk of such side effects necessitates close monitoring of the patients (e.g., liver function is tested monthly).

Another drug prescribed against hyperlipoproteinemia is clofibrate. The effectiveness of clofibrate also varies from subject to subject and its use is often accompanied by such side effects as nephrotic syndromes, myalgia, nausea and abdominal pain.

Diabetes

Diabetes, one of the most insidious of the major diseases, can strike suddenly or lie undiagnosed for years while attacking the blood vessels and nerves. Diabetics, as a group, are far more often afflicted with blindness, heart disease, stroke, kidney disease, hearing loss, gangrene and impotence. One third of all visits to physicians are occasioned by this disease and its complications, and diabetes and its complications are a leading cause of untimely death in the United States and in the Western world.

Diabetes adversely affects the way the body uses sugars and starches which, during digestion, are converted into glucose. Insulin, a hormone produced by the pancreas, makes the glucose available to the body's cells for energy. In muscle, adipose (fat) and connective tissues, insulin facilitates the entry of glucose into the cells by an action on the cell membranes. The ingested glucose is normally converted in the liver to $CO_2$ and $H_2O$ (50%); to glycogen (5%); and to fat (30-40%), the latter being stored in fat depots. Fatty acids from the adipose tissues are circulated, returned to the liver for re-synthesis of triacylglycerol and metabolized to ketone bodies for utilization by the tissues. The fatty acids are also metabolized by other organs. Fat formation is a major pathway for carbohydrate utilization.

The net effect of insulin is to promote the storage and use of carbohydrates, protein and fat. Insulin deficiency is a common and serious pathologic condition in man. In insulin-dependent (IDDM or Type I) diabetes the pancreas produces little or no insulin, and insulin must be injected daily for the survival of the diabetic. In noninsulin-dependent (NIDDM or Type II) diabetes the pancreas retains the ability to produce insulin and in fact may produce higher than normal amounts of insulin, but the amount of insulin is relatively insufficient, or less than fully effective, due to cellular resistance to insulin.

In either form of diabetes there are widespread abnormalities. In most NIDDM subjects, the fundamental defects to which the abnormalities can be traced are (1) a reduced entry of glucose into various "peripheral" tissues and (2) an increased liberation of glucose into the circulation from the liver. There is therefore an extracellular glucose excess and an intracellular glucose deficiency. There is also a decrease in the entry of amino acids into muscle and an increase in lipolysis. Hyperlipoproteinemia is also a complication of diabetes. The cumulative effect of these diabetes-associated abnormalities is severe blood vessel and nerve damage.

Other than the present invention and previous work by the present inventors (discussed below), no effective treatment has been found for controlling either hyperinsulinemia or insulin resistance. Hyperinsulinemia is a higher-than-normal level of insulin in the blood. Insulin resistance can be defined as a state in which a normal amount of insulin produces a subnormal biologic response. In insulin-treated patients with diabetes, insulin resistance is considered to be present whenever the therapeutic dose of insulin exceeds the secretory rate of insulin in normal persons. Insulin resistance is also associated with higher-than-normal levels of insulin i.e. hyperinsulinemia—when normal or elevated levels of blood glucose are present.

Previous Work of the Present Inventors

The present inventors and their co-workers have found that administration of certain prolactin inhibitors (e.g., dopamine agonists such as bromocriptine) and/or prolactin stimulators (e.g., dopamine antagonists, such as metoclopramide; serotonin agonists and precursors, such as 5-hydroxytryptophan) and particularly administration of such substances at predetermined times, reduce body fat stores, obesity, plasma triglycerides and cholesterol as well as hyperglycemia, hyperinsulinemia and insulin resistance: U.S. Pat. Nos. 4,659,715; 4,749,709; 4,783,469; 5,006,526 and PCT Application US92/11166.

Related Applications

Co-pending patent application Ser. No. 07/192,332 (now abandoned in favor of its Rule 62 continuation Ser. No. 999,685, abandoned in favor of application Ser. No. 08/287,066, now U.S. Pat. No. 5,496,803) discloses methods for regulating lipid metabolism disorders by administering prolactin (or both prolactin and a glucocorticosteroid ("GC")) into the bloodstream of an animal or human on a timed daily basis in an amount and for a period of time sufficient to modify and reset the neural phase oscillation of the prolactin daily rhythm. This modification was found to increase insulin sensitivity.

The prolactin (or prolactin and glucocorticosteroid) injections are timed to create a peak in the subject's daily prolactin (or both prolactin and glucocorticosteroid) profile that coincides in time with the peak prolactin level (or prolactin and GC peaks, respectively) of a lean, insulin-sensitive human in order to increase insulin sensitivity and reduce body fat stores. Injections of the same agent(s) are timed towards the peak prolactin level time of an obese subject to achieve fat gain in a lean subject, if desired.

Co-pending application Ser. No. 07/463,327 abandoned in favor of application Ser. No. 07/719,745, now U.S. Pat. No. 5,344,832, discloses a method of modifying and resetting the neural phase oscillations of both prolactin and GC in an obese animal by administering a dopamine agonist at a predetermined time of day such that the prolactin (and/or GC) peak(s) of the obese animal will be phase-shifted to coincide with those of a lean animal. This results in the reduction of at least one of body fat stores, body weight, hyperinsulinemia, hyperglycemia and/or the increase of insulin sensitivity.

Pirenzepine is not specifically disclosed in this or in the other applications discussed below. The property of pirenzepine of increasing HDL is also not disclosed.

In co-pending application Ser. No. 07/719,745 now U.S. Pat. No. 5,344,832 we have disclosed and claimed enhanced methods for modifying and resetting the phase as well as the amplitude of prolactin daily rhythms. These methods comprise both (a) administering to the subject a dopamine agonist just after the time at which the normal prolactin profile peaks to reduce prolactin levels to the low "day" levels and (b) administering to the subject a prolactin stimulator at a time before the prolactin level peaks in normal subjects to achieve or maintain a peak for prolactin at night-time. The objective of this treatment is alteration of the subject's prolactin level profile to mimic in shape and time the profile of a lean healthy human not suffering from one or more of these metabolic disorders.

Ser. No. 07/719,745 also discloses and claims the further administration of a thyroid hormone to subjects that are being treated with a dopamine agonist and prolactin stimulator, especially to those subjects that are chronically or seasonally hypothyroid.

Co-pending application Ser. No. 07/995,292 now U.S. Pat. No. 5,585,347 discloses methods for determining whether the daily circulating prolactin profile in a subject is abnormal, and methods for normalizing prolactin profiles found to be aberrant. In pertinent part, the treatment method involves administration of a prolactin inhibitor no later than the time at which during waking hours prolactin level in the subject to be treated is at its highest, and may also involve administration of a prolactin stimulator timed to cause a peak of prolactin level to occur during night-time. The objective of this treatment is alteration ("sculpting") of the subject's prolactin profile to mimic in shape and time the profile of a lean healthy human not suffering from any disorders.

Work of Third Parties

As far as the present inventors know, administration of pirenzepine or methyl scopolamine or other muscarinic, especially M1, receptor antagonists has not been used to combat obesity or atherosclerosis or hyperlipoproteinemia, or hyperlipidemia, or to increase HDL. Pirenzepine is marketed overseas as an anti-ulcer drug. The following publications relate to certain experiments involving pirenzepine and diabetes.

Atiea et al. *J. of Clin. Endocrinol.* 69:390–395 (1989) report the administration of pirenzepine to patients suffering from insulin-dependent (Type I) diabetes (IDDM). The goal of this treatment is to suppress nocturnal growth hormone (GH) secretion, as this hormone is believed to account for the early morning rise in glucose levels seen in Type I diabetics. Both acute (single dosage) and chronic administration was studied in conjunction with overnight low dose insulin infusion. In the acute study, two doses of 100 mg of pirenzepine were given at 2200 and 2400 hours, with measurement of plasma glucose, insulin, growth hormone, glucagon, cortisol, norepinephrine and epinephrine being made. The chronic study consisted of seven days of this treatment, with measurements being taken on the seventh night.

Pirenzepine treatment under both of the Atiea dosing regimes caused a reduction in plasma growth hormone concentrations. The authors also report an increase in plasma insulin concentration after seven days of pirenzepine treatment, a result which the authors tentatively attribute to a reduction in insulin clearance from the plasma. (It should be noted that other authors, such as Bevan—see below—report a decrease in plasma insulin in similar experiments conducted using Type II diabetics.)

The Atiea study relates the timing of administration of pirenzepine with the late nocturnal growth hormone release, which pirenzepine suppresses. The attendant decrease in morning levels of blood glucose is a direct effect of growth hormone suppression and is not related to modulation of insulin sensitivity or of lipogenic sensitivity. This reference therefore does not disclose or suggest any ability of pirenzepine to modulate either insulin sensitivity or lipogenic sensitivity.

Atiea et al. make no measurements of fat stores, or plasma lipid or lipoprotein concentrations and are silent as to any effect that pirenzepine could have on these values. The entire focus is on IDDM, which is a disorder distinct from NIDDM. Moreover, there is no suggestion that the treatment with pirenzepine could or would have long-term effects following cessation of its administration.

Martina et al. *J. of Clin. Endocrinol.* 68:392–396 (1989) report the results of chronic (one month) administration of pirenzepine to insulin-dependent (Type I) diabetics. The pirenzepine (100 mg) was administered orally once daily at 2300 hours.

Martina et al. report suppression of nocturnal GH secretion. Measured as area under the concentration curve, GH was reduced from 1407 to 877 µg/L*min. Nocturnal plasma glucose levels were reduced from a peak of about 6.5 µg/L at 0300 hours to about 2 µg/L at 0300 hours. This article states that early morning plasma glucose levels may have been reduced, because four of the thirteen patients studied had reduced insulin requirements, although the difference was not significant for the group as a whole.

This study relates its timing of administration of pirenzepine with the time of sleep (for reasons analogous to Atiea et al.) and makes no suggestion that this timing should be correlated with any other indicia, such as lipogenic activity. This reference does not disclose or suggest any ability of pirenzepine to interfere with lipogenic activity or with insulin sensitivity. Martina et al. make no measurements of plasma lipid or lipoprotein concentrations and are silent as to any effect that pirenzepine could have on these values.

Pietschmann et al. *Acta Endocrinol. (Copenh)* 117:315–319 (1988) report the effects of administering pirenzepine to patients suffering from Type I diabetes (IDDM). Two doses of pirenzepine (50 mg) were given orally in random order with a placebo at 2130, 0800, and 1200 hours. Plasma glucose, cortisol, insulin, and C-peptide were measured every three hours.

Both plasma glucose levels (10 mmol/L vs. 8 mmol/L at peak) and serum GH levels (6 µg/L vs. 3 µg/L at peak) were significantly lowered by the pirenzepine treatment. However, cortisol, insulin and c-peptide levels were unaffected by the treatment.

The effects of pirenzepine on blood glucose reported in the Pietschmann study are completely accounted for by the concomitant decrease in growth hormone. Furthermore, this study does not relate the timing of administration of pirenzepine with any particular time of the day, and makes no suggestion that this timing should be correlated with any other indicia, such as lipogenic activity. This reference does not disclose or suggest any ability of pirenzepine to produce long-term effects following the cessation of treatment. Pietschmann et al. make no measurements of fat stores, or plasma lipid or lipoprotein concentrations and are silent as to any effect that pirenzepine could have on these values or on insulin resistance.

Bevan et al. *Clinical Endocrinol.* 36:85–91 (1991) report effects of administration of pirenzepine to human subjects suffering from NIDDM. Five non-obese and five obese NIDDM patients were studied. Pirenzepine (200 mg) was given orally once, at 0800 hours, following an overnight fast. Breakfast was then given at 0900 hours, and measurements of plasma glucose and insulin were subsequently made.

Bevan et al. mention the correlation between hyperinsulinemia and coronary heart disease and suggest that pirenzepine could be used to treat obese NIDDM patients susceptible to high insulin values. However, Bevan do not measure nor report a change in fat, or in any of the other lipid metabolism parameters mentioned above. Furthermore, their experiment suggests only that pirenzepine lowers plasma glucose and insulin response after a meal. Bevan's observation of reduced insulin levels was not accompanied by a reduction of blood glucose (in fact blood glucose levels were slightly higher though the change was not significant). This means that insulin sensitivity was either unaffected (or that it may have been adversely affected if the blood glucose increases were significant).

Bevan administered pirenzepine only at 08:00 and therefore was not able to discern or to suggest any effects of the presence of pirenzepine in the blood at other times of the day.

The Bevan study relates the timing of administration of pirenzepine solely with the timing of a meal, and makes no suggestion that this timing should be correlated with any other indices, certainly not lipogenic sensitivity. This reference does not disclose or suggest any ability of pirenzepine to interfere with lipogenic sensitivity or insulin sensitivity (or even to affect basal insulin or glucose levels) or to instill a benefit that persists after cessation of therapy. Bevan et al. make no measurements of fat stores, or plasma lipid or lipoprotein concentrations and contain no data or suggestion that pirenzepine would have any effect on their values.

The results reported in Bevan et al., for NIDDM subjects can be attributed to the direct effects of pirenzepine on insulin and growth hormone production. Pirenzepine, by inhibiting cholinergic activity, acutely suppresses insulin secretion and accounts for the reduced insulin secretory response to a meal after a single dose of pirenzepine. The acute effects of pirenzepine would be to reduce growth hormone secretion and directly lower blood glucose concentration.

Pirenzepine antagonism of gastric and duodenal motility acts to slow absorption of a meal and therefore considerably blunts and delays the post-prandial rise in plasma glucose concentration, as seen in Bevan et al.

Coiro, V. et al., *Gen. Endocrinol. Invest.*, 1986, 9:27–30 report that pirenzepine (three doses during the day of 25 mg each and a fourth 50 mg dose two hours before glucose injection) did not alter basal glucose level and did not significantly increase blood glucose level after i.v. glucose administration in normal human subjects. At the same time, insulin release was reduced. As discussed with respect to Bevan et al. above, pirenzepine by inhibiting cholinergic activity suppresses insulin response to a glucose load. There is no suggestion in Coiro that insulin sensitivity has been increased and Coiro contains no disclosure nor inference about modulation of lipid metabolism.

All of the foregoing references (other than Bevan et al.) disclosing use of pirenzepine or methylscopolamine to modulate glucose metabolism involve either normal or insulin-dependent (Type 1, IDDM) diabetic subjects. All of these references teach the use of these M1 muscarinic receptor antagonists for their direct effect alone, i.e. for their ability to suppress growth hormone or to inhibit cholinergic activity and thereby suppress insulin. There is no teaching of either a short-term or long-term modulation of insulin sensitivity or lipid metabolism.

Thomas et al., *Sem. Hop. Paris* 53:1857–1862 (1977) discuss the effect of bromocriptine on diabetics. Bromocriptine (7.5 to 20 mg) is given daily by mouth. No timing is reported for administration.

The results of the treatment did not indicate particular efficacy, with six patients having improvement in glucose regulation, 4 having aggravation, and 14 showing no significant change. The results were not dependent on the type of diabetes or the patient age, but appeared to the authors to be more effective in patients who had been diabetic for a shorter time and who were less affected by diabetic retinopathy.

This reference does not mention the timing of the administration of the drug and does not suggest that timing would or could be important. Further, the reference does not report any effect on lipid regulation. There is also no suggestion to combine this treatment with any other drug treatment, such as pirenzepine.

Barnett et al., *Postgrad. Med. J.* 56:11–14 (1980) report effects of treatment of maturity onset (Type II) diabetes with bromocriptine or metoclopramide. Bromocriptine (2.5 mg) was administered once 2 hours prior to the glucose challenge. Plasma glucose, growth hormone, prolactin and insulin were measured at 15 minute intervals both before and after the glucose administration.

Bromocriptine treatment was found to decrease plasma glucose concentration, which was taken to indicate an improvement in glucose tolerance. Plasma insulin decrease with drug administration was significant. As expected, bromocriptine decreased markedly plasma prolactin levels.

The decrease in plasma glucose levels reported with Type II patients in this study was also significant. The authors hypothesized that glucose decrease may be due to bromocriptine's ability to reduce prolactin levels in these patients without an increase in growth hormone levels.

The Barnett reference does not disclose or suggest a continuing tratment with bromocriptine, nor a long-term modulation of plasma glucose via bromocriptine administration. Furthermore, the reference does not mention the importance of determining the timing of the administration of the drug and makes no mention of the ability of bromocriptine to affect lipogenesis or to have a long-term effect. There is also no suggestion to combine this treatment with any other drug treatment, such as pirenzepine. Finally, there is no mention of effects on fat stores, or plasma lipid or lipoprotein concentrations.

Poland, R. E. et al., 1989, *Biol. Psychiatry* 25:403–412 disclose that scopolamine (3.0 µ/kg and 6.0 µg/kg) was administered intramuscularly at 11:00 pm to eight normal male volunteers. Scopolamine produced a significant dose-related delay in rapid eye movement latency, but did not affect nocturnal plasma cortisol concentrations.

Davidson, M. B. et al., *Diabetes*, 1988, 37:166–171 discloses administration of a sleeping medication alone with five milligrams methscopolamine bromide to Type I diabetic patients at 2230 h resulting in marked inhibition of peak growth hormone (known to be a lipolytic and hyperglycemia-inducing agent) concentrations after sleep. Methscopolamine also caused the dawn effect (i.e. the increase in plasma glucose concentration observed in diabetics early in the morning) to decrease.

Grigoriev, A. I. et al., *Aviat. & Environ. Med.*, 1988, 59:301–305 disclose the administration of scopolamine (0.01 mg/kg given orally 2 hours before exposure to rotation) significantly decreased the susceptibility of normal subjects to motion sickness caused by rotation in moderate susceptibility subjects. However, time course variations of hormone concentrations (ACTH, cortisol, STH and prolactin) were identical between scopolamine and placebo receiving subjects.

Mendelson, W. B. et al., *J. Clin. Invest.*, 1978, 61:1683–1690 disclose administration of 0.5 mg methscopolamine bromide intramuscularly to normal subjects at 10:pm, ½ hour before bedtime. The drug dramatically reduced both overall growth hormone levels and mean peak growth hormone levels during the night but did not affect sleep patterns or insulin-induced hypoglycemia. The authors conclude that methscopolamine did not affect prolactin levels during sleep.

Curtis-Prior, P. B. et al., *Experientia*, 1979, 35:1430–1431 disclose that scopolamine hydrobromide did not significantly affect glycerol release from isolated fat cells (a lipolytic index) of rats in vitro nor inhibited adipose tissue cyclic AMP phosphodiesterase activity.

Östinson, C-G. et al., *Endocrinol.*, 1987, 121:1705–1710 disclose that fasting decreased the binding of the muscarinic antagonist methylscopolamine to pancreatic islet cells of non-diabetic rats. However, binding of methylscopolamine to islets of rats with diabetes (that serve as an animal model for IDDM) induced by streptozotocin (STZ, which destroys β-cells) was enhanced by 80% compared to binding to normal cells and that this increase was due to increased number of binding sites of the STZ islets. Insulin treatment of STZ rats lowered the binding of methylscopolamine. These results lead the authors to conclude that glycemia participates in the regulation of the number of muscarinic receptors expressed in pancreatic islet cells and this regulation is associated with changes in cholinergic-induced insulin secretion. These data indicate that methylscopolamine increases blood glucose concentration which would lead one to expect that methylscopolamine would exacerbate symptoms of diabetes.

Davidson, M. B. et al., *Diabetes Care* 1990, 13:813–814 disclose that methscopolamine bromide suppressed sleep induced growth hormone secretion and attenuated the dawn phenomenon when given at bedtime. Chronic use of 5 mg of methylscopolamine bromide was not particularly well tolerated by most patients and, according to the authors, this therapy did not "appear to be a clinically useful approach to achieving euglycemia."

Davis, B. M. et al., *Psychoneuroendocrinology*, 1982, 7:347–354 report that administration of methscopolamine (0.5 or 0.75 milligrams subcutaneously) decreased the elevated AVP, cortisol and prolactin levels of subjects that experience unpleasant side effects after administration of physostigmine. Methscopolamine also inhibited growth hormone secretion.

Risch, S. C. et al., *Psychoneuroendocrinology*, 1986, 11:221–230 report that muscarinic receptor antagonist methscopolamine inhibited the affect of physostigmine on plasma concentrations of pituitary hormones including cortisol, prolactin, adrenocorticotropic hormone (ACTH) and others.

The administration of pirenzepine or methyl scopolamine (or other muscarinic M1 receptor antagonists) optionally in combination with bromocriptine (or another dopamine agonist or other substance that reduces plasma prolactin levels) for affecting lipogenesis and ameliorating symptoms of lipid metabolism disorders and Type II diabetes according to the present invention has not been previously disclosed. Nor has it been proposed to use such muscarinic receptor antagonists (alone or in conjunction with dopamine agonists) at predetermined times during a 24-hour period to reduce lipogenesis or lipogenic activity, or to improve glucose metabolism. Further, these uses of muscarinic and particularly M1 receptor antagonists in countering hyperlipoproteinemias by increasing the HDL fraction of lipoproteins has also not been previously disclosed, and is an aspect of the presently claimed invention. Additionally, the use of these antagonists to reduce over the long term (even after cessation of treatment) body fat stores or plasma lipid concentration (and thereby combat atherosclerosis) has not been proposed before the present invention.

OBJECTS OF THE INVENTION

It is one object of this invention to provide improved methods for reducing in vertebrate subjects (including humans) in need of such treatment at least one of body fat stores, hyperlipidemia, hyperlipoproteinemia, and for abating atherosclerosis. Another object is to provide improved methods for reducing at least one of insulin resistance, hyperinsulinemia, and hyperglycemia and abating Type II diabetes. It is another object of this invention to provide methods for interfering with lipid and glucose metabolism in a manner beneficial to the host.

It is yet another object of this invention to provide improved methods for the long-term reduction and abatement of at least one of the foregoing disorders based on a therapeutic regimen administered over the short-term.

It is still another object of the present invention to provide a method for regulating, and altering on a long term basis, the lipogenic and glucose responses of vertebrate animals, including humans.

In particular, it is an object of the invention to provide methods for producing long lasting beneficial changes in one or more of the following: the amount of body fat stores, the sensitivity of the cellular response of a species to insulin (reduction of insulin resistance), blood insulin levels, hyperinsulinemia, blood glucose levels, blood lipoprotein levels, and thus to provide effective treatments for obesity, atherosclerosis and/or diabetes.

SUMMARY OF THE INVENTION

At least one of the foregoing objects is accomplished by:

(a) A method that involves administration to a vertebrate subject in need of such treatment of pirenzepine, or methyl scopolamine or another muscarinic (preferably M1) receptor antagonist in an amount effective to improve one or more aberrant indices associated with lipid metabolism disorders (e.g., obesity, high cholesterol, hyperlipidemia, hyperlipoproteinemia).

(b) Another method that involves administration to a vertebrate in need of such treatment of pirenzepine or methyl scopolamine or another muscarinic (preferably M1) receptor antagonist at a predetermined time during a 24-hour period and in an amount effective to improve one or more aberrant indices associated with glucose metabolism disorders (e.g., glucose intolerance, insulin resistance, hyperglycemia, hyperinsulinemia and Type II diabetes) and/or with lipid metabolism disorders (such as those mentioned above). Continuing this therapy for a period of time causes the improvements to persist after cessation of therapy.

(c) Yet another method involves administration to a vertebrate subject in need of such treatment of a muscarinic M1 receptor antagonist in combination with a prolactin inhibitor (such as a d2 dopamine agonist) to improve aberrant indices associated with lipid and/or glucose metabolism disorders.

(d) Finally, another method that involves the administration to a vertebrate in need of such treatment of a muscarinic M1 receptor antagonist alone or in combination with a prolactin inhibitor, each being administered at a predetermined time to accomplish improvements in the foregoing lipid and/or metabolic disorders. Continuing this therapy for a period of time causes these improvements to persist after cessation of therapy.

The long-term persisting effects described in (b) and (d) above are referred to as the "indirect effects" of muscarinic M1 receptor antagonists (alone or in combination with prolactin inhibitors), and are attributed to resetting of circadian rhythms, more specifically neural phase oscillators in the central nervous system.

BRIEF DESCRIPTION OF THE FIGURE

FIG. 1 is a graph of average plasma-prolactin levels (ng/ml) for "healthy" individuals (males: "M" curve; females: "F" curve) v. time of day (hours).

DETAILED DESCRIPTION OF THE PREFERRED EMBODIMENTS

All patents, patent applications and literature references cited herein are incorporated by reference in their entirety as if their disclosures were physically present in the present specification. In case of conflict, however, the present disclosure controls.

Vertebrate animals include without limitation humans and other mammals (e.g. domestic animals, laboratory animals and pets) and avians.

The Direct Effect—Timed Administration for Altering Lipid and Glucose Metabolism The direct effect of pirenzepine or methyl scopolamine or other muscarinic M1 receptor antagonists in reducing one or more of body fat stores, blood lipids, blood lipoproteins (LDL, VLDL and chylomicrons) and increasing HDL/LDL or improving the HDL/LDL ratio, can be accomplished by administering to a vertebrate animal in need of such treatment from about 0.1 to about 10 mg/kg/day (preferably 0.7 to 5 mg/kg/day) of pirenzepine or about 0.01 to about 5 mg/kg/day (preferably 0.1 to 5 mg/kg/day) of methyl scopolamine. Other M1 receptor antagonists with similar pharmacokinetic properties are anticipated to be used at comparable amounts on a molar basis. The amounts of yet other M1 receptor antagonists will have to be adjusted based on their individual pharmacokinetic properties. Furthermore, it is expected that the amount of each compound will be subject to optimization but this will involve no more than routine experimentation.

It is preferred that a muscarinic M1 receptor antagonist be administered at a predetermined time during a 24-hour period designed to reduce lipogenic response in the subject to be treated during a time "window" or "interval" in which the particular subject's lipid metabolism is responsive to the treatment (compared to the remainder of the 24-hour period). The amounts of M1 receptor antagonist used in this "timed" administration are generally the same as described above. Effectiveness of the administration at a particular time is assessed by such indices as triglyceride level, body fat, cholesterol level, VLDL level etc.

Glucose metabolism can be altered, and symptoms associated with type II diabetes can be decreased or eliminated, in accordance with a "timed" administration of M1 receptor antagonists wherein one or more appropriate indices for glucose metabolism and/or type II diabetes can be used to assess effectiveness of the treatment (dosage and/or timing): e.g. glucose tolerance, glucose level, insulin level, insulin sensitivity, glycosylated hemoglobin.

An effective time for administering an M1 muscarinic receptor antagonist needs to be identified. This can be accomplished by routine experiment as described below, using one or more groups of animals (preferably at least 5 animals per group).

In animals, lipogenic inhibition by M1 receptor antagonist treatment can be assessed by administering the antagonist at a particular time of day and measuring the effect of the administration (if any) by measuring one or more indices associated with lipogenesis (Meier, A. H., Am. J. Physiol., supra, 1977 or Cincotta, A. H. et al Horm. Metabol. Res., supra, 1989), and comparing the post-treatment values of these indices to the values of the same indices prior to treatment. A convenient first time for administering the M1 receptor antagonist is towards the beginning of the daily activity period of the host.

If the time chosen is effective in decreasing lipid metabolism indices, the experimentation can stop. If the results of the administration are not satisfactory, then the search for an appropriate administration time should continue as follows: The M1 receptor antagonist can be administered to the same (or preferably another) group of animals at a different time of day and the same indices can be measured, and compared to the first set of lipogenic index values and/or to a pretreatment set of lipogenic index variables. The second test time of administration is preferably 6–12 hours earlier (or later) than the first test administration time. Based on the difference in index values, the second test time can be selected as the time of therapy, or another (third) test time of administration can be selected by interpolation (or extrapolation). For example, if a third time were selected in Example 3 or 4 it could have been around 1400. At most, this time-ascertaining experiment would need to be conducted four times. The duration of each test treatment is 2–14 days.

The same procedure can be followed for determining an effective time of administration for affecting glucose metabolism, i.e. a time of administration during the glucose metabolism responsiveness "window" or "interval". The present inventors have also found that M1 muscarinic receptor antagonists have more pronounced beneficial effects on aberrant glucose metabolism if administered at certain predetermined times (which may but need not be the same as the preferred times for altering lipid metabolism) during a 24-hour period. Again, a first test time of administration is selected and a test administration is conducted for 2–14 days. If the result is not satisfactory (based on comparison of the values of pretreatment and post-treatment glucose metabolic indices) a second administration time is selected (and optionally a second group of animals is tested), and so on as described above for treatment of lipid metabolism aberrations.

The approach for determining an effective time of administration in a human is basically the same: A M1 muscarinic receptor antagonist is administered daily to a human in need of lipid (or glucose) metabolism modification at a first time of day for 2–14 days, preferably a week. The relevant metabolic indices are measured prior to, during, and after treatment. Measurement of these indices is preferably made at the same time of day (between 14:00 and 22:00).

If the treatment selected is effective, the time of the test administration is adopted as the time of treatment for the human.

If the time selected is not effective (i.e. produces no significant change, or produces an adverse change in the relevant metabolic parameter or par&meters) then administration at this time is immediately discontinued and a different time is selected (6–12 hours before or after the first time). The test treatment and metabolic index measurement is then repeated.

It should be noted that the time of light onset and duration of daylight as well as the age, sex and physical condition and the activity/rest regimen of the subject to be treated will influence the time or times at which administration of M1 muscarinic receptor antagonist will be effective. It is thus preferred to ascertain an effective administration time for each individual, using the above-described method.

The amount of pirenzepine/methyl scopolamine (or other muscarinic receptor antagonist) to be used depends in part on the duration of the increased lipid metabolism responsiveness (or glucose metabolism responsiveness) interval or window and in part on the half-life of the compound used. For example pirenzepine has a half-life of about 11 hours, while methyl scopolamine has a shorter half-life of about 4–6 hours.

The precise time of administration and/or amount of muscarinic receptor antagonist that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

While the subject is being treated, lipid or glucose metabolism is monitored by measuring one or more of the relevant indices at predetermined times during a 24-hour period. Treatment (amounts, times of administration and type of medication) may be adjusted (optimized) according to the results of such monitoring. The patient is periodically reevaluated to determine extent of improvement by measuring the same parameters, the first such reevaluation typically occurring at the end of four weeks from the onset of therapy, and subsequent reevaluations occurring every 4 to 8 weeks during therapy and then every 3 months thereafter. Therapy may continue for several months or even years with six months being a typical length of therapy for humans.

Adjustments to the amount(s) of drug(s) administered and possibly to the time of administration may be made based on these reevaluations. For example, if after 4 weeks of treatment one of the metabolic indices has not improved but at least one other one has, the dose could be increased by ⅓ without changing the time of administration.

Adjustments will be further modified and fine-tuned on an individual basis and with reference to the pharmacokinetics of the agent used.

In most cases, adjustment of timing and amount of drug(s) is not considered necessary if the results (i.e. amelioration of the metabolism disorder or disorders involved) are positive, i.e. if a clinically significant improvement has been achieved.

In treating vertebrates, generally, dosages of one or more muscarinic receptor antagonists, respectively, are each given, typically over a period ranging from about 10 days to about 180 days. Some patients (e.g. patients in particularly poor physical condition, or those of an advanced age) may require a longer, or even continuous, treatment with a muscarinic receptor antagonist.

In the practice of this invention, an M1 receptor antagonist is administered daily to a subject preferably orally, or by subcutaneous, intravenous or intramuscular injection. Dermal delivery systems e.g., skin patches, as well as suppositories and other well-known systems for administration of pharmaceutical agents can also be employed.

Timed treatment with an M1 receptor antagonist can have the added benefit of decreasing cholesterol levels, while increasing HDL levels. As discussed above, such an alteration is highly desirable to reduce the risk of a subject to development of atherosclerosis and subsequent heart disease.

Suitable muscarinic receptor antagonists include substances that directly or indirectly block activation of muscarinic cholinergic receptors. Preferably, such substances are selective (or are used in amounts that promote such selectivity) for the M1 receptor. Nonlimiting examples include quaternary amines (such as methantheline, ipratropium, and propantheline), tertiary amines (e.g. dicyclomine, scopolamine) and tricyclic amines (e.g. telenzepine). Pirenzepine and methyl scopolamine are preferred. Other suitable muscarinic receptor antagonists include benztropine (commercially available as COGENTIN from Merck), hexahydro-sila-difenidol hydrochloride (HHSID hydrochloride disclosed in Lambrecht, et al., *Trends in Pharmacol. Sci.* 10(Suppl):60, 1989; (±)-3-quinuclidinyl xanthene-9-carboxylate hemioxalate (QNX-hemioxalate; Birdsall et al., *Trends in Pharmacol. Sci.* 4:459, 1983; telenzepine dihydrochloride (Coruzzi, et al., *Arch. Int. Pharmacodyn. Ther.* 302:232, 1989 and Kawashima et al., *Gen. Pharmacol.* 21:17, 1990) and atropine. The dosages of such muscarinic receptor antagonists will be generally subject to optimization as outlined above. In the case of lipid metabolism disorders, dosage optimization may be necessary independently of whether administration is timed by reference to the lipid metabolism responsiveness window or not.

Combination of Muscarinic Receptor Antagonist and Prolactin Inhibitor—Direct Effect In terms of regulating insulin and lipid metabolism and reducing the foregoing disorders, M1 receptor antagonists (e.g. pirenzepine and methyl scopolamine) act synergistically with prolactin inhibitors such as d2 dopamine agonists (e.g. bromocriptine) or certain prolactin inhibiting ergo alkaloids.

In the practice of this aspect of the invention, a M1 receptor antagonist (such as pirenzepine) alone or in combination with a prolactin-inhibiting compound (e.g., a d2 dopamine agonist such as bromocriptine or a prolactin-inhibiting ergot alkaloid compound) are administered daily to a subject preferably orally, or by subcutaneous, intravenous or intramuscular injection. Dermal delivery systems e.g., skin patches, as well as suppositories and other well-known systems for administration of pharmaceutical agents can also be employed. Appropriate time(s) for administration and amounts administered can be identified as outlined above for the "direct effect" of muscarinic receptor antagonists. Alternatively, the time and amount for the prolactin inhibitor can be determined as outlined in related application Ser. No. 07/995,292, incorporated by reference.

Suitable prolactin inhibitors include without limitation prolactin-inhibiting ergo alkaloids and prolactin-inhibiting dopamine agonists. Examples of suitable compounds include 2-bromo-alpha-ergocriptine, 6-methyl-8 beta-carbobenzyloxyaminoethyl-10-alpha-ergoline, 8-acylaminoergolines, 6-methyl-8 -alpha-(N-acyl)amino-9-ergoline, 6-methyl-8 alpha-(N-phenylacetyl)amino-9-ergoline, ergocornine, 9,10-dihydroergocornine, D-2-halo-6-alkyl-8-substituted ergolines, D-2-bromo-6-methyl-8-cyanomethylergoline, carbidopa, benserazide and other dopadecarboxylase inhibitors, L-dopa, dopamine and non toxic salts thereof.

Effective amounts of prolactin inhibitor for humans are generally within the range of 0.4–5.0 mg/day, typically within the range of 0.8–5.0 mg/day if the inhibitor is bromocriptine (and an equivalent molar amount based on activity, bioavailability and half-life if another prolactin inhibitor is used).

Effective amounts of prolactin inhibitors for vertebrates generally are within the range of about 3 to about 40 micrograms per pound body weight per day.

The "Indirect" Effect

The synergism of prolactin inhibitors and muscarinic (M1) receptor antagonists is expected to be also present in the following aspect of the present invention, which takes advantage of the "indirect" effect of these substances.

Another aspect of the invention is directed to administration of an M1 receptor antagonist (e.g. pirenzepine) either alone or in conjunction with a prolactin inhibitor (e.g. bromocriptine) to produce long term; lasting, or even permanent effects on lipid and glucose metabolism by the administration of timed daily dosages to a vertebrate, animal or human, of a M1 muscarinic receptor antagonist, either alone or in conjunction with bromocriptine or another d2 dopamine agonist (or other prolactin inhibitor). The dosages are continued on a daily basis for a period sufficient to reset the phase of at least one major neuroendocrine circadian rhythm (e.g., the central neural oscillator expressed by the circadian rhythm of circulatory prolactin) in the subject being treated, in that the phase and amplitude of the prolactin rhythm is modified to resemble that for a healthy, lean, young subject of the same species (and, if applicable, of the same sex), i.e. moves closer to that depicted in FIG. 1. The window of increased responsiveness of the subject's lipid or glucose metabolism can thus be related to the prolactin level daily rhythm of the subject. Essentially, any change in secretion, or blood level, of any hormone or other phenomenon which occurs in a circadian pattern and constitutes an expression of a central neural oscillation can be used to monitor alterations in the central neural oscillation it expresses. Resetting of circadian rhythms occurs if the administration of the muscarinic receptor antagonist alone or in conjunction with the prolactin inhibitor is continued for a period of time, generally at least about 10 days, preferably several months (e.g. typically 6 months for humans). Resetting has occurred if the beneficial effect(s) on the glucose/lipid metabolism persist on a long-term basis (e.g. months or even years) after the drug(s) is (are) discontinued.

These and other features of the invention will be better understood by reference to the experiments described in the examples below. In the examples the terminology "LD" refers to the light/dark cycle, the first number following the expression LD refers to the hours of light, and the second to the hours of darkness in the cycle. Thus, LD 14:10 refers to a cycle having 14 hours of light and 10 hours of darkness, and the period of a day is expressed in terms of 2400 hours. "BW" designates body weight, g represents grams, and mg represents milligrams.

All reagents and materials are commercially available. It should be noted that the Sprague-Dawley rat is a good, reliable model for both obesity and insulin resistance conditions in humans.

EXAMPLES 1 AND 2

Effects of Pirenzepine Administration without Regard to Timing on Various Metabolic Indices in Male Sprague-Dawley Rat For each experiment, two groups of 8-9 Male Sprague-Dawley rats (5 mos. of age, exp. 1; 4 mos. of age, exp. 2) were provided with either untreated rodent chow (Purina) or rodent chow supplied with pirenzepine (Sigma Chemical, St. Louis, Mo.) ad libitum. The approximate amount of pirenzepine consumed was 2.5 mg/kg BW/day. Following 18 days of treatment, the rats were fasted for six hours and then sacrificed two hours prior to the offset of light (LD 12:12) when blood samples and fat indices were taken. Plasma total cholesterol, triglycerides and glucose were determined utilizing diagnostic kits supplied by Sigma Chemical. Plasma HDL cholesterol was determined with a kit also obtained from Sigma Chemical after phosphogentisic acid precipitation of other lipoproteins. Plasma insulin concentration was determined utilizing a double-antibody radioimmunoassay kit-available from ICN Biochemicals (Irvine, Calif.). Food consumption was monitored at regular 3-day intervals throughout the study. The results from these experiments are contained in Table 1 (P=pirenzepine; C=control).

TABLE 1

Effects of Pirenzepine Supplied in the Food on Various Metabolic Indices in Male Sprague-Dawley rats[1]

| | Expt. 1 | | Expt. 2 | |
|---|---|---|---|---|
| | C | P | C | P |
| Retroperitoneal fat (g) | 3.01 ± 0.23 | 2.27 ± 0.04* | 4.36 ± 0.40 | 2.99 ± 0.27* |
| Plasma Cholesterol (mg/dL) | 97.6 ± 9.1 | 61.2 ± 3.4* | 104.3 ± 6.2 | 104.4 ± 4.0 |
| Plasma HDL Cholesterol (mg/dL) | | | 39.9 ± 2.2 | 55.6 ± 2.4* (139.4% of control) |
| Plasma Triglyceride (mg/dL) | | | 110.3 ± 12.6 | 74.9 ± 17.1 |
| Plasma Glucose (mg/dL) | | | 159.9 ± 6.6 | 140.5 ± 4.4* |
| Plasma Insulin (mg/dL) | | | 143.0 ± 7.2 | 104.1 + 5.3* |

[1]Values represented are means ± standard error of the mean.
*Differs significantly from control group (P < 0.05).

In Examples 1 and 2, the supply of pirenzepine was through the food and consequently pirenzepine was available throughout the day. These experiments therefore measure the effect of constantly available pirenzepine on the measured metabolic indices. In Experiments 1 and 2, administration of pirenzepine through the food supply resulted in a significant reduction in retroperitoneal body fat. Experiment 1 also resulted in a significant decrease in total plasma cholesterol. This effect was not observed in Experiment 2, however, significant decreases in total plasma cholesterol have been repeatedly documented in later experiments, such as those reported in Example 3. In Experiment 2, HDL cholesterol, triglyceride, plasma glucose, and plasma insulin were measured. The significant increase in plasma HDL is particularly notable, while both plasma glucose, and plasma insulin were significantly decreased. Triglyceride was also reduced; however, due to high standard error, these decreases cannot be considered statistically significant based on these data. Importantly, food consumption was no different between control and pirenzepine-fed animals in either experiment.

Because pirenzepine was available in the food throughout the day, Experiments 1 and 2 cannot account for differences in efficacy of pirenzepine dependent on timing of the administration. These have been illustrated in subsequent experiments, described in the following examples.

EXAMPLE 3

Strategically Timed Effects of Pirenzepine on Various Metabolic Indices in Male Sprague-Dawley Rats Two groups of young male Sprague-Dawley rats (3 mos of age, 7-8 per group) were provided an oral dose of pirenzepine (2.5 mg/kg BW/day in 1 ml of peanut butter) at the onset or offset of light (LD 12:12, lights on at 7:00). One ml of peanut butter alone was administered at the alternative time of day. A third group (control, 12 rats) was provided with 1 ml of peanut butter alone at both the onset and offset of light. After three weeks of treatment, blood samples were taken every eight hours over a twenty-four hour period beginning at offset of light (19:30) in order to obtain overall daily mean concentrations of the parameters measured. The rats were fasted for six hours prior to blood sampling, sacrifice and retroperitoneal fat measurement. Analyses were performed according to the methods described for Examples 1 and 2, above. The results of this experiment are contained in Table 2.

TABLE 2

Timed Effects of Pirenzepine on Various Metabolic Indices in Male Sprague-Dawley rats[1]

| | Control | Pirenzepine 0800 | Pirenzepine 1930 |
|---|---|---|---|
| Retroperitoneal fat (g) | $1.66 \pm 0.14^2$ | $1.55 \pm 0.26$ | $1.29 \pm 0.05^a$ |
| Plasma Cholesterol (mg/dL) | $76.6 \pm 3.2$ | $66.10 \pm 3.6^a$ | $65.5 \pm 3.9^a$ |
| Plasma HDL Cholesterol (mg/dL) | $36.4 \pm 0.9$ | $41.5 \pm 2.1^a$ | $43.1 \pm 2.7^a$ (118.4% of control) |
| Plasma Triglyceride (mg/dL) | $185.3 \pm 13.5$ | $143.3 \pm 12.1^a$ | $120.5 \pm 6.6^a$ |
| Plasma Glucose (mg/dL) | $124.4 \pm 3.4$ | $130.2 \pm 4.2$ | $125.9 \pm 6.1$ |
| Plasma Insulin (uU/mL) | $175.0 \pm 4.4$ | $99.0 \pm 3.4^a$ | $56.3 \pm 4.5^{ab}$ |

[1]food consumption did not differ between treated and control rats, nor with treatment timing.
[2]mean ± standard error of the mean.
[a]Differ significantly from controls ($P < 0.05$).
[b]Differ significantly from other experimental (timed pirenzepine) group ($P < 0.05$).

In contrast to Examples 1 and 2, the experiment reported in Example 3 was designed to test for differences in effectiveness of pirenzepine based on time of administration. Two times were selected (according to the guidelines provided earlier in the present specification) to target pirenzepine treatment either within (1930, called a "strategic" time) or away (0800, called a "random" time) from the thus determined interval of increased lipid metabolism responsiveness to pirenzepine in the Sprague-Dawley rat.

In Example 3, both "random" and "strategic" administration of pirenzepine resulted in significant decreases in total plasma cholesterol, plasma triglyceride and plasma insulin. "Strategic" timed administration also resulted in a significant decrease in retroperitoneal body fat. Both "random" and "strategic" administrations also resulted in significant increases in plasma HDL. The dramatic reduction (68%) in plasma insulin concentration with the "strategic" pirenzepine treatment time was not associated with any increase in plasma glucose concentration and indicates an increase in sensitivity of the tissues to insulin action (i.e., a decrease in insulin resistance). These results highlight the importance of selection of administration time and indicate a correlation between the time of administration, lipogenesis, and effect on lipid and glucose metabolic indices.

EXAMPLE 4

Long-Term Effects of Timed Pirenzepine and Methyl Scopolamine Administration

Forty male older Sprague-Dawley rats (6 months of age) were separated into 5 groups of 8 rats each. Two of the groups received an oral dose of pirenzepine (P) (4 mg/kg b.w., Sigma, in 1 ml peanut butter) daily at either 0800 or 1800 (LD 12:12, lights on 0700). Another 2 groups received an oral dose of methylscopolamine bromide salt (M) (500 µg/kg b.w., Sigma, in 1 ml peanut butter) daily at either 0800 or 1800. A control group (C) received peanut butter only daily at 0800 and 1800. Rat chow (Purina) was made available ad libitum. Treatment lasted two weeks. Blood samples were taken-and retroperitoneal fat was dissected and weighed 18 days after the last day of treatment. This made it possible to assess long term effects of the treatment. Two-three animals from each group were sacrificed every eight hours beginning at the offset of light. All animals were fasted 6 hours prior to blood sampling and sacrifice. Plasma triglyceride, total cholesterol, and HDL-cholesterol (phosphogentisic acid precipitation method) were measured utilizing kits obtained from Sigma Chemical, as described above.

As in Example 3, the time of pirenzepine and methylscopolamine administration had a dramatic effect on lipid and glucose metabolism (Table 3). The most effective time of administration for both drugs for these rats was also early in the light period (0800) as indicated by significantly reduced retroperitoneal body fat, plasma lipid indices, and improved insulin resistance (decreased plasma insulin and glucose concentrations 18 days post-treatment). Interestingly, these beneficial effects were accomplished in conjunction with a significant increase in food consumption. Although an increase in HDL-cholesterol was seen only with drug administration at 1800, it is anticipated that further refinement of administration time would target one or more optimal times for each or all of these indices. It should also be noted that the rats used in Example 3 were substantially older than those used in Examples 1 and 2.

These results represent a long-term effect of both pirenzepine and methylscopolamine on improving symptoms associated with Type II diabetes that persist long after treatment is discontinued. Further experiments (data not shown) have confirmed persistence of the long-term effect for a period of time in excess of three months.

TABLE 3

Timed Effects of Pirenzepine and Methylscopolamine on Various Metabolic Indices

| | Food Consumption g/day | Triglyceride (mg/dL) | Cholesterol (mg/dL) | HDL-Chol (mg/dL) | Retroperitoneal Fat (g) | Plasma Insulin | Plasma Glucose |
|---|---|---|---|---|---|---|---|
| C | $14.3 \pm 0.7$ | $105.6 \pm 4.6$ | $138.6 \pm 2.1$ | $51.0 \pm 2.3$ | $3.02 \pm 0.21$ | $159 \pm 9$ | $172 \pm 5$ |
| P 0800 | $17.7 \pm 1.2^b$ | $73.3 \pm 2.9^{a,c}$ | $71.9 \pm 2.0^{a,c}$ | $42.2 \pm 1.9^{a,c}$ | $2.36 \pm 0.18^a$ | $127 \pm 12^{a,c}$ | $140 \pm 6^{a,c}$ |

TABLE 3-continued

Timed Effects of Pirenzepine and
Methylscopolamine on Various Metabolic Indices

| | Food Consumption g/day | Triglyceride (mg/dL) | Cholesterol (mg/dL) | HDL-Chol (mg/dL) | Retroperitoneal Fat (g) | Plasma Insulin | Plasma Glucose |
|---|---|---|---|---|---|---|---|
| M 0800 | 17.5 ± 1.3[b] | 90.0 ± 3.1[a,c] | 96.8 ± 1.8[a,c] | 43.9 ± 2.7[a,c] | 2.18 ± 0.31[a] | 118 ± 7[a,c] | 158 ± 4 |
| P 1800 | 15.8 ± 0.8 | 181.6 ± 4.0[b,c] | 94.4 ± 1.6[a,c] | 62.4 ± 1.8[b,c] | 2.57 ± 0.12 | 168 ± 11[c] | 183 ± 6[c] |
| M 1800 | 14.9 ± 1.0 | 188.0 ± 5.7[b,c] | 133.6 ± 1.9[c] | 61.0 ± 1.9[b,c] | 2.61 ± 0.19 | 171 ± 14[c] | 148 ± 7[a] |

[a]Significantly less (p < 0.05) than control
[b]Significantly more (p < 0.05) than control
[c]Time of administration made significant difference (p < 0.05)

In Table 3, "P" designates pirenzepine, "M" designates methylscopolamine, and "C" designates control.

EXAMPLE 5

Synergistic Effect of M1 Muscarinic Receptor Antagonist and D2 Dopamine Agonist

Adult female Syrian Hamsters (10 weeks old, approximately 155 g BW) born and raised on 14 h daily photoperiods were transferred to 10 h daily photoperiods and injected with either saline (control), bromocriptine (200 µg/animal), methscopolamine (20 mg/kg BW), pirenzepine (20 mg/kg BW), bromocriptine (200 µg/animal) plus methscopolamine (20 mg/kg BW), or bromocriptine (200 µg/animal) plus pirenzepine (20 mg/kg BW) daily for eight weeks.

Following eight weeks of treatment, animals were subjected to a glucose tolerance test and blood samples were taken for the analyses of plasma glucose and insulin levels (expressed as area under curve, "AUC" in Table 4) before and at 30, 60, 90 and 120 minutes after the injection (i.p.) of glucose (2.0 g/kg BW). All injections were administered at 9 HALO.

Animals were sacrificed by sodium pentobarbital overdose and retroperitoneal fat pads were removed and weighed as an index of body fat level.

TABLE 4

| Treatment | n | body wt (g) | body fat pad wt (g) | AUC/Glucose mg % (hr) | AUC/Insulin µU/ml (hr) |
|---|---|---|---|---|---|
| control | 6 | 214 ± 7 | 8.7 ± 0.4 | 516 ± 22 | 550 ± 26 |
| bromo. | 6 | 182 ± 9* | 6.0 ± 0.4* | 474 ± 36 | 265 ± 80* |
| methscop. | 5 | 206 ± 6 | 7.2 ± 0.4 | 495 ± 31 | 373 ± 26* |
| pirenz. | 6 | 192 ± 9 | 7.1 ± 0.6 | 440 ± 31 | 359 ± 75* |
| bromo. & methscop. | 5 | 179 ± 5* | 4.0 ± 0.4*[abc] | 317 ± 56[abc] | 154 ± 29*[abc] |
| bromo. & pirenz. | 6 | 179 ± 4* | 4.7 ± 0.3*[abc] | 432 ± 53 | 235 ± 24*[bc] |

An asterisk in Table 4 denotes a significant difference from control at P<0.05 (Student's t test). The notation "a" denotes a significant difference from the group treated with bromocriptine alone; "b" denotes a significant difference from the group treated with methylscopolamine alone; and "c" denotes a significant difference from the group treated with pirenzepine alone.

The effect of the bromocriptine and methscopolamine combination is considered synergistic with respect to body fat, glucose and insulin because these are biological indices which were already considerably decreased with one drug.

EXAMPLE 6

Synergistic Effect of M1 Antagonist and Prolactin Inhibitor

Adult female Syrian Hamsters (10 wks old; 155 g BW) born and raised on 14 h daily photoperiods were transferred to 10 h daily photoperiods and injected i.p. with either saline (control), bromocriptine (200 µg/animal), methscopolamine (1 mg/kg BW) or bromocriptine (200 µg/animal) plus methscopolamine (1 mg/kg BW) for eight weeks. All injections were given at 9 HALO. At the end of treatment, animals were sacrificed by sodium pentobarbital. Fat pads were removed and weighed as an index of body fat. The results are reported at Table 5.

TABLE 5

| Treatment | n | body wt (g) | body fat pad wt (g) |
|---|---|---|---|
| neg. control | 6 | 203 ± 3 | 7.6 ± 0.6 |
| bromo. | 6 | 184 ± 7* | 5.2 ± 0.4* |
| methscop. | 5 | 201 ± 9 | 5.8 ± 0.4 |
| bromo. & methscop. | 6 | 189 ± 7 | 4.2 ± 0.3*[ab] |

In the above table, an asterisk denotes a significant difference from the negative control (P<0.5; Student's t test); Superscript "a" denotes a significant difference from treatment with bromocriptine alone and superscript "b" denotes a significant difference from treatment with methyl scopolamine alone. Thus, body fat decrease pursuant to combination treatment is considered a synergistic result.

EXAMPLE 7

Timed Administration of Methyl Scopolamine

Methylscopolamine (MSC) (0.5 mg/kgBW) in 1 mL peanut butter was fed at light onset (AM) or at light offset (PM) to 9 Sprague-Dawley rats (30 weeks old) in each group daily for two weeks. Nine other rats were fed only peanut butter. 18 days after the last treatment, the rats were sacrificed and the indices in Table 6 were measured.

TABLE 6

Long-term Effects of Treatment With Timed Administration of Methylscopolamine on Retroperitoneal Body Fat and Various Metabolic Indices

|  | Control | MSC(AM) | MSC(PM) |
|---|---|---|---|
| Retroperitoneal Fat (g) | 3.75 ± 0.18 | 2.78 ± 0.08* | 2.45 ± 0.07* |
| Triglycerides (mg/dL) | 199 ± 1.8 | 197 ± 18 | 106 ± 21§ |
| Glucose (mg/dL) | 213.7 ± 8.3 | 151.8 ± 19.6* | 147/2 ± 17.2* |
| Cholesterol (mg/dL) | 107.3 ± 6.5 | 94.7 ± 4.9 | 94.1 ± 5.7 |
| HDL Cholesterol (mg/dL) | 38.5 ± 2.7 | 32.5 ± 4.1 | 45.2 ± 4.2§ |
| Insulin (μU/mL) | 189.3 ± 7.9 | 144.1 ± 5.9* | 163.8 ± 2.7*§ |

*significant difference with respect to control
§significant difference with respect to other experimental group The results in Table 6 show that MSC significantly reduced retroperitoneal fat, glucose and insulin whether administered at light onset or offset. MSC significantly reduced triglycerides and increased HDL only when administered at light offset. Furthermore, light-offset administered MSC significantly reduced triglycerides and insulin and significantly increased cholesterol compared to light-onset administered MSC.

The results in Table 6 also show that administration of methylscopolamine for a period of time has a long-term effect that persists after cessation of the treatment.

The invention has been described above by reference to specific embodiments. It is apparent that in the practice of the present invention various modifications, additions and omissions can be made without departing the spirit and scope of this invention, as claimed below.

What is claimed is:

1. A method of treating Type II diabetes in a mammalian subject in need of such treatment comprising administering to said subject an amount of a muscarinic receptor antagonist selective for the M1 receptor at a predetermined time during a 24-hour period, said amount and said time being effective to accomplish at least one of: decreasing hyperinsulinemia, decreasing hyperglycemia, and decreasing insulin resistance in said subject.

2. The method of claim 1 wherein said subject is human.

3. The method of claim 1 wherein said antagonist is selected from the group consisting of:
methantheline, ipratropium, propantheline, dicyclomine, scopolamine, methylscopolamine, telenzepine, benztropine, QNX-hemioxalate, hexahydro-siladifenidol hydrochloride and pirenzepine.

4. The method of claim 3 wherein said antagonist is selected from the group consisting of pirenzepine and methyl scopolamine.

5. The method of claim 2 wherein said antagonist is selected from the group consisting of:
methantheline, ipratropium, propantheline, dicyclomine, scopolamine, methylscopolamine, telenzepine, benztropine, QNX-hemioxalate, hexahydro-siladifenidol hydrochloride and pirenzepine.

6. The method of any one of claims 1-4 and 5, said administration of said antagonist taking place at a predetermined time within a 24-hour period at which the glucose or lipid metabolism of said mammal is responsive to said antagonist.

7. The method of claim 1 wherein said M1 muscarinic antagonist is administered at a single predetermined time.

8. The method of claim 1 wherein said administration is continued for a period of at least 10 days up to about 180 days.

* * * * *